US00PP30652P2

(12) United States Plant Patent
Tuszyński

(10) Patent No.: US PP30,652 P2
(45) Date of Patent: Jul. 2, 2019

(54) ***CORDYLINE* PLANT NAMED 'TUS019'**

(50) Latin Name: *Cordyline australis*
Varietal Denomination: Tus019

(71) Applicant: Grzegorz Tuszyński, Otrebusy (PL)

(72) Inventor: Grzegorz Tuszyński, Otrebusy (PL)

( * ) Notice: Subject to any disclaimer, the term of this patent is extended or adjusted under 35 U.S.C. 154(b) by 72 days.

(21) Appl. No.: 15/732,088

(22) Filed: Sep. 14, 2017

(51) Int. Cl.
*A01H 5/12* (2018.01)

(52) U.S. Cl.
USPC ..... Plt./383
CPC ..... *A01H 5/12* (2013.01)

(58) Field of Classification Search
USPC ..... Plt./383
See application file for complete search history.

(56) References Cited

PUBLICATIONS

UPOV hit on *Cordyline* plant named 'TUS019', QZ PBR 20161708, filed Jul. 5, 2016.*

* cited by examiner

*Primary Examiner* — Anne Marie Grunberg
(74) *Attorney, Agent, or Firm* — Penny J. Aguirre

(57) ABSTRACT

A new cultivar of *Cordyline australis*, 'Tus019', characterized by its varigated foliage with a blend of dark pinkish brown-green centers and bright pink margins and streaks, and its ascading growth habit.

2 Drawing Sheets

Botanical classification: *Cordyline australis.*
Cultivar designation: 'Tus019'.

CROSS REFERENCE TO A RELATED APPLICATION

This application is related to a European plant breeders' rights application filed on Jul. 5, 2016, application No. 2016/1708. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Cordyline australis* and will be referred to hereafter by its cultivar name, 'Tus019'. 'Tus019' represents a new cultivar of cabbage tree or cabbage palm and is grown as a foliage plant for landscape and container use.

The new cultivar was discovered as a naturally-occuring chimeral mutation by the Inventor in Otrebusy, Poland in January of 2016 of *Cordyline australis* 'Red Star' (not patented) that was growing in a container.

Asexual propagation of the new cultivar was first accomplished by tissue culture using meristemac tissue by the Inventor in Otrebusy, Poland in 2016. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Tus019' as a new and unique cultivar of *Cordyline.*

1. 'Tus019' exhibits varigated foliage with a blend of dark pinkish brown-green centers and bright pink margins and streaks.
2. 'Tus019' exhibits a cascading growth habit.

The parent plant of 'Tus019', 'Red Star' differs from 'Tus019' in having reddish brown foliage with no variegation. 'Tus019' can be most closely compared to the *Agapanthus* cultivars 'Charlie Boy' (U.S. Plant Pat. No. 20,139) and 'Seipin' (U.S. Plant Pat. No. 19,927). 'Charlie Boy' and 'Seipin' are similar to 'Tus019' in foliage variegation. 'Charlie Boy' differs from 'Tus019' in having leaf centers that are more brown in color and center foliage that is more upright. 'Seipin' differs from 'Tus019' in having leaf centers that is greyed-brown in color and center foliage that is more upright.

BRIEF DESCRIPTION OF THE DRAWINGS

The accompanying colored photographs illustrate the overall appearance and distinct characteristics of the new *Cordyline*. The photographs were taken of a 6 month-old plant of 'Tus019' as grown in a 3-liter container in a greenhouse in Boskoop, The Netherlands.

The photograph in FIG. 1 provides a side view of a plant of 'Tus019'.

Figure 1:
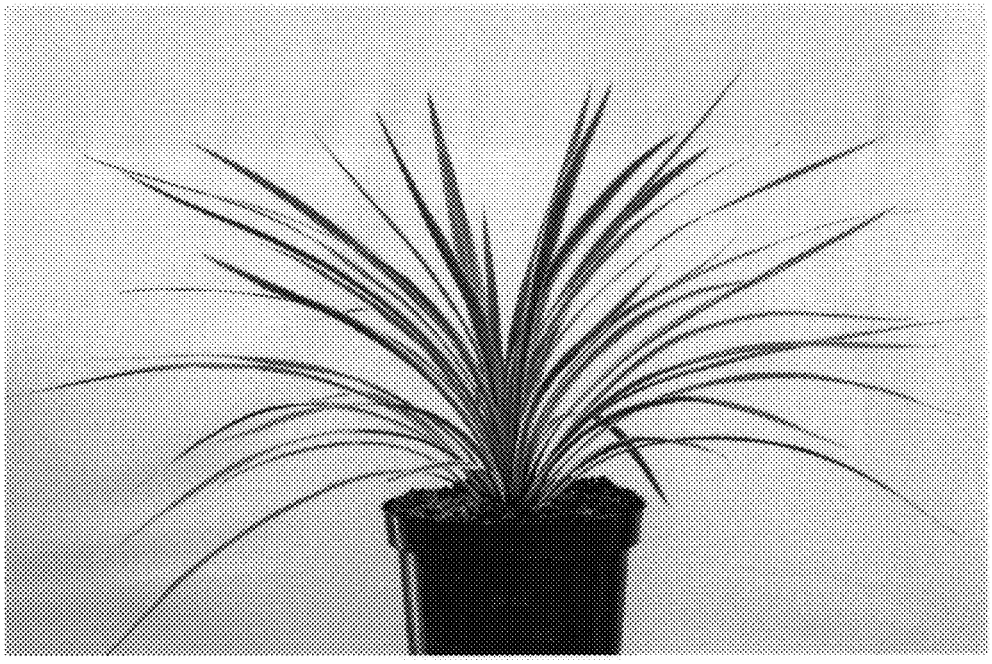
Figure 2:
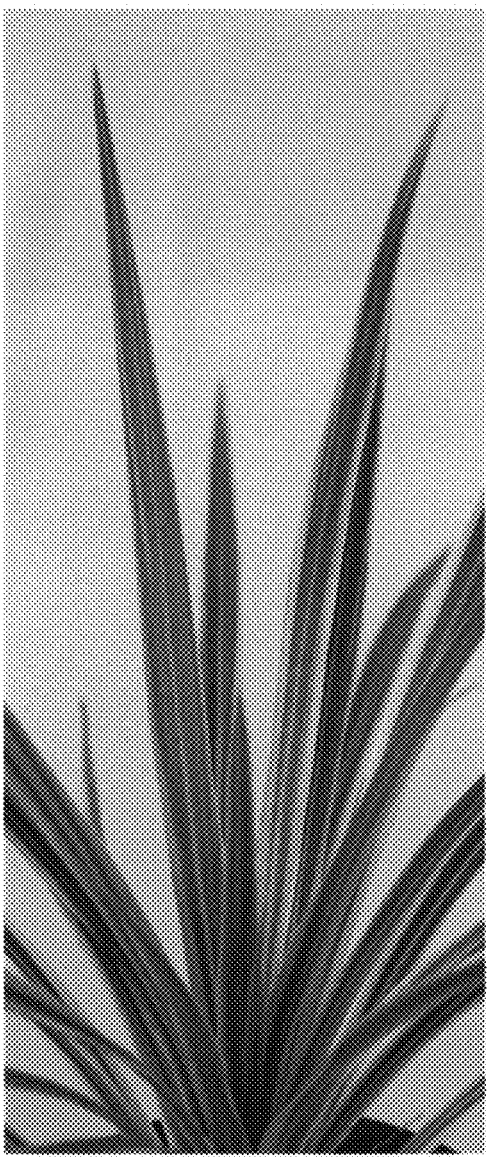

The photograph in FIG. 2 provides a close-up view of the foliage of 'Tus019'.

The colors in the photographs are as close as possible with the photographic and printing technology utilized and color values cited in the detailed botanical description accurately describe the colors of the new *Cordyline.*

DETAILED BOTANICAL DESCRIPTION OF THE PLANT

The following is a detailed description of plants six months in age as grown in 3-liter containers in a greenhouse in Boskoop, The Netherlands. The phenotype of the new cultivar may vary with variations in environmental, climatic, and cultural conditions, as it has not been tested under all possible environmental conditions. The color determinations are in accordance with The 2015 R.H.S. Colour Chart of The Royal Horticultural Society, London, England, except where general color terms of ordinary dictionary significance are used.

General description:

*Plant type*.—Perennial.

*Plant habit*.—Initially upright with prodominently cascading foliage.

*Plant size*.—Average of 32.3 cm in height and 72 cm in spread as a 6 month-old plant as grown in a 3-liter container.

*Blooming period*.—No flower production observed.

*Hardiness*.—At least in U.S.D.A. Zones 8 to 12.

*Diseases and pests*.—No susceptibility to resistance to diseases or pests has been observed.

*Root description*.—Fibrous.

*Propagation*.—Tissue culture.

*Growth rate*.—Moderate.

*Root development*.—In tissue culture; an average of 3 weeks for root initiation and 12 to 16 weeks to produce a fully rooted young plant.

Stem description: Main shoot grows from base, no stems present.

Foliage description:

*Leaf shape*.—Linear.

*Leaf division*.—Simple.

*Leaf quantity*.—47.

*Leaf base*.—Sheathing, sheath length; average of 1.2 cm in length, 1 cm in width and 157D in color.

*Leaf apex*.—Narrow and long acuminate, outer tip mucronate (not sharp to the touch).

*Leaf venation*.—Parallel, only main vein visible, upper surface color; a blend of 166A, 177A, N199A to N199B and 200B, axially striped with a blend of 43C, 43D, 52B, 52C, 179B and 179C, lower surface color; between 152A and N199A.

*Leaf margins*.—Entire, smooth, unlobed.

*Leaf arrangement*.—Alternate and rosulate.

*Leaf aspect*.—Flat to very slightly carinate and slightly arching, held at multiple angles.

*Leaf surface*.—Texture upper and lower surface; glabrous and smooth and non-rugose, upper surface glossy, lower surface very slightly glossy.

*Leaf color*.—Young upper surface; a blend of 178A, 178B, 183A, 183B and 183C, axially striped between 180D and 181C, young lower surface; between 183B and 200B, axially striped 180A and 180B, mature upper surface; a blend of 166A, 177A, N199A, N199B and 200B, axially striped 43C, 43D, 52B, 52C, 179B and 179C, mature lower surface; a blend of 177A and 200C, axially striped 52B, 52C and 180C.

*Leaf size*.—Average of 40.3 cm in length and 1.4 cm in width.

*Petiole*.—None present.

It is claimed:

1. A new and distinct cultivar of *Cordyline* plant named 'Tus019' as herein illustrated and described.

* * * * *